US012775177B2

(12) United States Patent
Legerton et al.

(10) Patent No.: US 12,775,177 B2
(45) Date of Patent: Oct. 27, 2026

(54) SCLERAL CONTACT LENS

(71) Applicant: SHENYANG KANGENDE MEDICAL SCIENCE AND TECHNOLOGY CO., LTD., Shenyang (CN)

(72) Inventors: Jerome A. Legerton, Jupiter Inlet Colony, FL (US); Jidong Liu, Shenyang (CN); Gaozhi Liu, Shenyang (CN)

(73) Assignee: Shenyang Kangende Medical Science and Technology Co., Ltd., Liaoning (CN)

( * ) Notice: Subject to any disclaimer, the term of this patent is extended or adjusted under 35 U.S.C. 154(b) by 0 days.

(21) Appl. No.: 18/529,985

(22) Filed: Dec. 5, 2023

(65) Prior Publication Data

US 2024/0118561 A1 Apr. 11, 2024

Related U.S. Application Data

(62) Division of application No. 17/913,078, filed as application No. PCT/CN2021/107636 on Jul. 21, 2021, now Pat. No. 11,977,278.

(51) Int. Cl.
*G02C 7/00* (2006.01)
*A61B 3/107* (2006.01)
(Continued)

(52) U.S. Cl.
CPC ................ *G02C 7/04* (2013.01); *A61B 3/107* (2013.01); *A61F 9/013* (2013.01); *G02C 7/047* (2013.01);
(Continued)

(58) Field of Classification Search
CPC ...... A61B 3/107; A61F 9/013; A61F 9/00804; A61F 2009/00882; G02C 7/04; G02C 7/047; G02C 7/049
(Continued)

(56) References Cited

U.S. PATENT DOCUMENTS 5,452,031 A * 9/1995 Ducharme ............... G02C 7/04 451/64
5,929,968 A 7/1999 Cotie et al.
(Continued)

FOREIGN PATENT DOCUMENTS

CN 106842613 A 6/2017
CN 208270873 U 12/2018
(Continued)

OTHER PUBLICATIONS

PCT International Search Report and the Written Opinion mailed Feb. 24, 2022, issued in related International Application No. PCT/CN2021/107636 (8 pages).
(Continued)

*Primary Examiner* — Mahidere S Sahle
(74) *Attorney, Agent, or Firm* — Law Offices of Damon L. Boyd, PLLC

(57) ABSTRACT

In general, one aspect disclosed features a scleral contact lens for an eye of a patient, the scleral contact lens comprising: an anterior surface; and a posterior surface, the posterior surface comprising: a central optic zone defined by a base curve according to an apical radius of the cornea of the eye; a peripheral corneal zone peripheral to the central optic zone, a clearance control zone peripheral to the optic zone, and a scleral landing zone peripheral to the clearance control zone, the scleral landing zone having a single surface shape.

12 Claims, 9 Drawing Sheets

(51) Int. Cl.

| | |
|---|---|
| ***A61F 9/013*** | (2006.01) |
| ***G02C 7/02*** | (2006.01) |
| ***G02C 7/04*** | (2006.01) |
| *A61F 9/008* | (2006.01) |

(52) U.S. Cl.
CPC .......... *G02C 7/049* (2013.01); *A61F 9/00804* (2013.01); *A61F 2009/00882* (2013.01)

(58) Field of Classification Search
USPC ........................................ 351/159.02–159.38
See application file for complete search history.

(56) References Cited

U.S. PATENT DOCUMENTS

| | | | | |
|---|---|---|---|---|
| 2011/0153012 | A1* | 6/2011 | Legerton .................. | G02C 7/04 351/159.23 |
| 2013/0314665 | A1 | 11/2013 | Tung | |
| 2016/0349535 | A1 | 12/2016 | Creighton | |
| 2017/0123230 | A1* | 5/2017 | Carrasquillo .......... | G02C 7/047 |
| 2019/0155053 | A1* | 5/2019 | Sindt ................ | B29D 11/00961 |
| 2021/0149218 | A1* | 5/2021 | Mikaelian .............. | G02C 7/047 |
| 2023/0221581 | A1 | 7/2023 | Legerton et al. | |

FOREIGN PATENT DOCUMENTS

| | | | |
|---|---|---|---|
| CN | 110426861 | A | 11/2019 |
| CN | 212364749 | U | 1/2021 |
| CN | 112394539 | A | 2/2021 |
| CN | 113031307 | A | 6/2021 |
| CN | 113924070 | A | 1/2022 |
| WO | 2017/149512 | A1 | 9/2017 |
| WO | 2018/055220 | A1 | 3/2018 |

OTHER PUBLICATIONS

PCT International Preliminary Report on Patentability mailed Mar. 16, 2022, issued in related International Application No. PCT/CN2021/107636 (17 pages).

Non-Final Office Action mailed May 16, 2023, issued in related U.S. Appl. No. 17/913,078 (13 pages).

Final Office Action mailed Aug. 25, 2023, issued in related U.S. Appl. No. 17/913,078 (13 pages).

First Search dated Dec. 15, 2023, issued in related Chinese Patent Application No. 202180007707.3 (3 pages).

* cited by examiner

SCLERAL CONTACT LENS

CROSS REFERENCE TO RELATED APPLICATIONS

This application is a divisional application of U.S. patent application Ser. No. 17/913,078, filed on Sep. 20, 2022, entitled "Scleral Contact Lens", which is a national stage application under 35 U.S.C. § 371 of International Application No. PCT/CN2021/107636, filed on Jul. 21, 2021, entitled "Scleral Contact Lens." The entire contents of the above-identified applications are incorporated herein by reference.

DESCRIPTION OF RELATED ART

The disclosed technology relates generally to an ophthalmic device, and more particularly some embodiments relate to a scleral contact lens and methods for determining the parameters of the scleral contact lens.

BACKGROUND

Rigid contact lenses were commercialized more than 60 years ago. Initial fitting concepts quickly evolved to bi-curve and tri-curve designs in an attempt to facilitate the required lens movement for tear exchange in lenses that were not gas permeable. Lens movement with the blink was imperative to allow a fresh tear layer to move from the tear meniscus at the lower lid to beneath the lens. The simple lathes used in the first two decades of commercialization allowed for a central base curve and concentric peripheral curves having longer radii of curvature than the central base curve. The surfaces were blended to avoid sharp junctions in the location where two zones of unequal radii joined.

The central radius of the lens, also known as the base curve radius, was selected in relationship to the central corneal curvature. The base curve radius could be equal to, greater than, or shorter than the central corneal curvature based on the philosophy of the design. The radius of the first concentric zone (secondary curve) was always greater than the base curve radius and the radius of each consecutive zone peripheral to the more medial zone was also respectively greater than the radius of the zone just medial to it. Lenses historically had three or more zones. All zones outside the central optic zone were, as a rule, greater in radius than the underlying corneal radius. This was a requirement to facilitate lens movement and tear exchange.

Lenses of these designs demonstrated movement with the blink and with lateral eye movement. The lens movement was as much as 1.0 to 1.5 mm. Adaptation was required to become accustomed to the movement. Edge design was also very important to achieve comfort and prevent trauma to the bulbar and palpebral conjunctiva.

The advent of gas permeable materials reduced the need for the high degree of movement and the need for as much radial and axial edge lift that was required in non-gas permeable lenses. Even so, the traditional design concepts were perpetuated and used with the new materials. Over time, the rigid gas permeable lenses were designed to have less peripheral clearance and less movement. In the original designs made in non-gas permeable materials it was common to have a secondary curve radius that was of the order of 1.4 mm longer than the base curve radius while in the gas permeable designs the secondary curve radius trended toward 0.8 mm longer than the base curve radius. The mean difference of the base curve radius from the central corneal radius also trended in the shorter direction.

The mean overall diameter also trended in the larger direction with higher oxygen permeability of the rigid materials. As a result, the modal modern gas permeable lens is larger and more closely aligned with the cornea. Early polymethyl methacrylate (PMMA) lenses were designed to have axial edge lift approaching 100 microns while modern lenses may have as little as 50 microns of axial edge lift. Modern gas permeable lenses also demonstrate movement of the order of 0.25 mm or less as compared to 1.0 to 1.5 mm in early PMMA lenses.

Even so, the design concepts and teaching continue to use concentric zone features and their respective modulation in width and radius. Lenses and design programs refer to zones with regard to their width and local radii. Education curricula teach the modulation in terms of making the radii "flatter" or "steeper" and "narrower" or "wider". Since there exists no precise metrology for measuring the actual clearances of lenses and since the determination of the fit is by way of on-eye sodium fluorescein observations, the assessment of the fit is a learned art rather than a science.

Market dynamics demand efficient time management in the fitting of contact lenses. Chair time must be reduced and first-time success rates are an important metric for productivity in the field. The intention and purpose of this design is to reduce the selection of a final lens to a single parameter and to decrease the chair time required to achieve a proper lens prescription. An additional market factor is resident in the changes in the curriculum for ophthalmic professionals consistent with the integration of treatment of disease. The time allowed in the curriculum for contact lens education and training continues to reduce. Basic training is the objective of the programs and specialty training is regarded as a post graduate exercise. As a result, lens fitting concepts must be simple and must demand less training for a successful outcome.

The rigid gas permeable industry has transformed with the proliferation of mini-scleral and larger semi-scleral and scleral lenses. Full corneal diameter rigid gas permeable lenses are also commercialized (approximately 12 mm). All scleral lenses are ideally designed to allow no corneal contact. In fact, corneal contact often leads to mechanical trauma, staining, and epithelial defects when it occurs with scleral lenses. Full corneal diameter rigid gas permeable lenses have high and ideally uniform corneal contact with no scleral contact.

A number of scleral contact lens designs exist which control corneal clearance by way of selection of base curve radius or in combination with secondary zone geometry that includes tangent angles, third order polynomials, and curves with conics. The peripheral "landing zones" include concave to the eye curves, un-curved tangential, and convex to the eye curves that are co-axial or controlled by an angle. Many designs continue to be comprised of concentric co-axial concave to the eye curves consistent with the oldest designs of scleral and corneal contact lenses.

U.S. Pat. Nos. 8,113,653 and 8,113,652 teach scleral contact lens surfaces with meridional sagittal variation and methods for making and using convex to the eye curves controlled by an angle. The radius of curvature of the convex to the eye landing zone of respective products is of the order of 12 mm to 20 mm convex to the eye. The geometry of the landing zone with radii of this dimension requires control by modulating the angle to accommodate the diversity of the local slope of the sclera of eyes to be fit with scleral contact lenses. Methods of communicating such curves controlled by an angle is taught in U.S. Pat. No. 8,801,175.

Scleral contact lens products commonly have four or more zones. Each zone may vary in width, depth, and geometry and requires an independent parameter selection to obtain the proper apical clearance, peripheral corneal clearance, limbal clearance, and landing zone alignment over the sclera. The parameters may differ by meridian or semi meridian.

Instruments are commercialized for measuring the ocular contour. Even so very few instruments for measuring ocular contour are in use throughout the world. Methods of teaching multiple clinical observations are taught to mitigate the widespread absence of instruments for measuring ocular contour. For example, the application WO2017149512—SYSTEMS AND METHODS FOR FITTING CONTACT LENSES teaches the use of multiple antecedent clearance preferences and multiple clearance observations and a calculator is presented to assist the clinician in determining final lens parameters for each zone from known parameters of a predicate lens used to make the clearance observations.

A product opportunity exists for a scleral contact lens design that safely demonstrates easily controlled full corneal and limbal clearance while having proper landing on the sclera just outside the corneal-scleral junction (limbus). Unfortunately, the standard design paradigm of using concentric curves of ever-increasing radii would result in a lens having the contact at an undesired incident angle to the bulbar conjunctiva covering the sclera. Such a design would risk creating changes in the scleral shape and would also raise the probability of staining and mechanical trauma.

While attempts are made to manage the amount of scleral strain while achieving full limbal clearance, the precision and ability to experience consistency in fitting is questionable and high lens re-reorder rates are reported in the professional literature. Inconsistent scleral alignment and failure to have full limbal clearance is frequent given the low prevalence of instruments used to measure the ocular contour at key chords outside those measured by corneal topographers.

SUMMARY

Scleral contact lenses were the first examples of contact lenses for human use in the 19th century to solve the great need for optical correction of eyes having irregular corneal surfaces from trauma and disease. Modern materials and manufacturing methods facilitated a resurgence in the use of scleral contact lenses. Even so, the lack of instrumentation for measuring ocular contour leads to excessive time consumption for eye care practitioners along with high reorder rates due to low first fit success rates. Final success rates are reported to be less than 60% for seasoned commercialized products. There is a need for a simplified design that reduces the time required to reach successful fitting of scleral contact lenses along with reducing the training and know how required to fit scleral contact lenses and to mitigate the absence of instrumentation for measuring ocular contour.

The fitting objectives for scleral contact lenses include full corneal and limbal clearance without excessive clearance that stimulates bubble formation, and a circumferential lens to eye contact with the sclera that is free of excessive edge lift and free of impingement to the conjunctiva at the medial aspect of the scleral landing zone or at the lens edge. Contemporary lens designs and fitting methods require selection of parameters for multiple zones of a scleral contact lens based on observations of clearance or bearing in multiple zones of the lenses relative to the ocular surface.

Fortuitously, clinical observations of correlations of peripheral corneal elevation relative to apical corneal curvature supports an algorithm for empirically designing a second annular zone of scleral contact lenses in the absence of contour data. Clinical observations also support the regulation of the volume within a third annular zone of scleral contact lenses related to the depth of the zone. The deeper the zone the greater the need to decrease the volume of the zone and the shallower the zone the greater the need to increase the volume of the zone.

Embodiments of the disclosed technology provide for a novel universal scleral landing zone that eliminates the need to tediously manage the radius of the landing zone or the angle of incidence of the landing zone whether it is convex to the eye, uncurved or concave to the eye. The present invention provides for a universal landing zone based on the known depth of conjunctival compression with scleral contact lenses and the predetermined width of a scleral landing zone. The short effective radius of the convex to the eye scleral landing zone of the present invention deviates substantially from commercialized designs. The theory and practice with this short effective convex to the eye radius design supports that it has potential for use on a majority of eyes. Such use eliminates the need for the instrumentation for measuring ocular contour and reduces the need for training and know-how by eye care professionals who need and want to prescribe scleral contact lenses.

In general, one aspect disclosed features an ophthalmic device to be worn on the ocular surface with contact only outside the cornea, comprising: a rigid gas permeable material configured to the ocular contour of the respective eye of the user and to provide optical correction. The device may be applied to the surface of the eye and worn to provide optimum vision, comfort and health to the eye and adnexa of the user as a result of its design, material, manufacturing and methods of parameter selection.

In some embodiments the scleral contact lens is designed empirically from usual and customary clinical measurements. In other embodiments the parameters are selected from a single clinical observation of an initial lens having known parameters applied to the surface of an eye.

The problem solved by the present invention is the elimination of the need to select the parameters of multiple zones of a scleral contact lens by way of multiple clinical observations of clearances between the posterior surface of a predicate lens and the anterior surface of the eye or the need to have instrumentation for measuring the ocular contour of the eye or to measure impressions of an eye to derive the surface profile of a scleral contact lens for the eye from the contour of the Impression.

The present invention teaches an empirically derived Peripheral Corneal Zone based on the radius of curvature of a central Optic Zone; a volume-controlled Clearance Control Zone wherein the volume is modulated based on the sagittal depth of the zone; and a universal Scleral Landing Zone having a single convex to the eye radius of curvature that is not controlled by modulating an angle.

In general, one aspect disclosed features a scleral contact lens for an eye of a patient, the scleral contact lens comprising: an anterior surface; and a posterior surface, the posterior surface comprising: a central optic zone defined by a base curve according to an apical radius of the cornea of the eye; a peripheral corneal zone peripheral to the central optic zone, a clearance control zone peripheral to the optic zone, and a scleral landing zone peripheral to the clearance control zone, the scleral landing zone having a single surface shape for each overall lens diameter.

Embodiments of the scleral contact lens may include one or more of the following features. the base curve of the optic zone is defined by at least one of a spherical radius, an aspherical radius with a conic constant, a torus, a multifocal shape, or a rotationally asymmetric shape. In some embodiments, wherein the peripheral corneal zone, the clearance control zone, and the scleral landing zone are defined by a spline having a plurality of knots and/or control points. In some embodiments, the peripheral corneal zone is defined by a peripheral most knot and a medial most knot; wherein the peripheral most knot is shallower in sagittal depth than the medial most knot relative to a continuation of the base curve to the semi-chord diameter of the peripheral most knot when the base curve radius is shorter than a predetermined length; and wherein the peripheral most knot is deeper in sagittal depth than the medial most knot relative to the continuation of the base curve to the semi-chord diameter of the peripheral most knot when the base curve radius is longer than the predetermined length. In some embodiments, the predetermined length is 8.0 mm. In some embodiments, the clearance control zone is defined by at least one knot within the clearance control zone; wherein a location of the at least one knot is selected to control an area between the posterior surface of the clearance control zone and the underlying surface of the eye in at least one semi-meridian. In some embodiments, a convex to the eye radius of the scleral landing zone is less than 10 mm. In some embodiments, the scleral landing zone is defined by at least one knot of a spline that is equivalent in depth to a convex to the eye radius of less than 10 mm. In some embodiments, the scleral landing zone is defined by at least one knot of a spline that is equivalent in depth to a convex to the eye radius of less than 5 mm.

In general, one aspect disclosed features a method for defining a shape of a posterior surface of a scleral contact lens for an eye of a patient, the method comprising: defining a base curve for a central optic zone of the scleral contact lens according to an apical radius of the cornea of the eye; defining a peripheral corneal zone peripheral to the central optic zone; defining a clearance control zone peripheral to the optic zone; and defining a scleral landing zone peripheral to the clearance control zone according to a single surface shape.

Embodiments of the method may include one or more of the following features. Some embodiments comprise defining the base curve of the optic zone according to at least one of a spherical radius, an aspherical radius with a conic constant, a torus, a multifocal shape, or a rotationally asymmetric shape. Some embodiments comprise defining the peripheral corneal zone, the clearance control zone, and the scleral landing zone according to a spline having a plurality of knots and/or control points. In some embodiments, defining the peripheral corneal zone according to a peripheral most knot and a medial most knot; wherein the peripheral most knot is shallower in sagittal depth than the medial most knot relative to a continuation of the base curve to the semi-chord diameter of the peripheral most knot when the base curve radius is shorter than a predetermined length; and wherein the peripheral most knot is deeper in sagittal depth than the medial most knot relative to the continuation of the base curve to the semi-chord diameter of the peripheral most knot when the base curve radius is longer than the predetermined length. In some embodiments, the predetermined length is 8.0 mm. Some embodiments comprise defining the clearance control zone according to at least one knot within the clearance control zone; and selecting a location of the at least one knot to control an area between the posterior surface of the clearance control zone and the underlying surface of the eye in at least one semi-meridian. In some embodiments, a convex to the eye radius of the scleral landing zone is less than 10 mm. Some embodiments comprise defining the scleral landing zone according to at least one knot of a spline that is equivalent in depth to a convex to the eye radius of less than 10 mm. Some embodiments comprise defining the scleral landing zone according to at least one knot of a spline that is equivalent in depth to a convex to the eye radius of less than 5 mm.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

Figure 1:
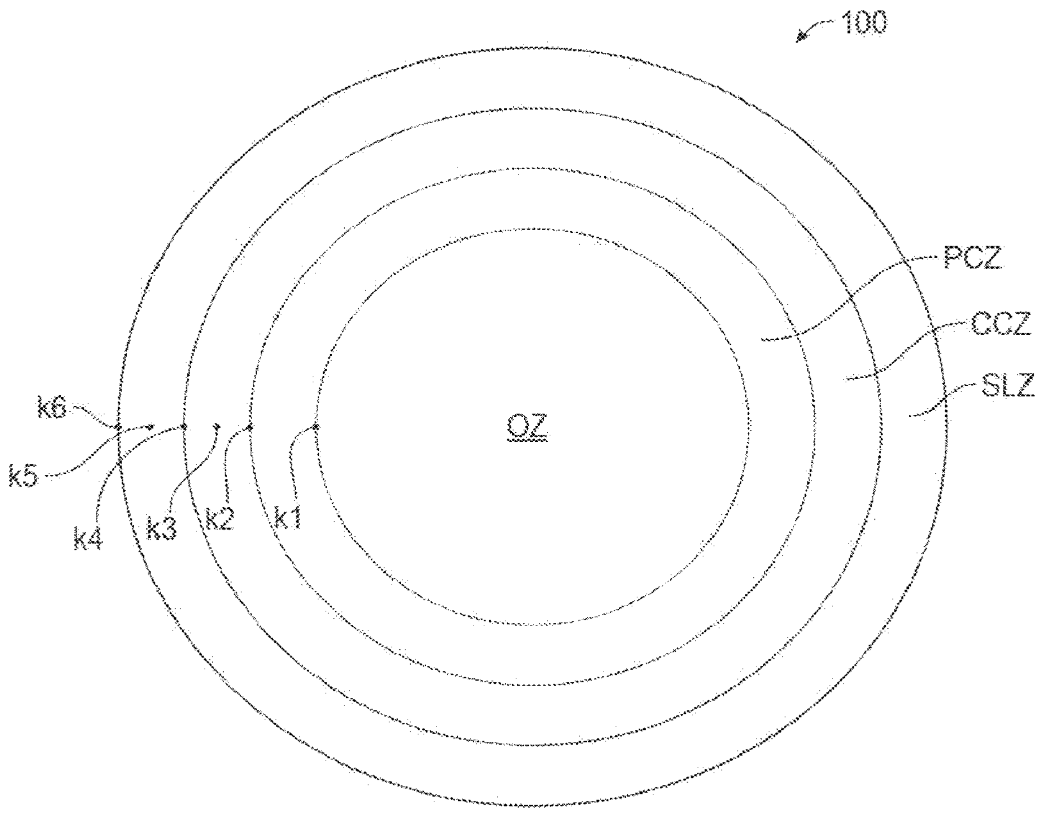
FIG. 1 is a front view of a scleral contact lens of the present invention with knots and zones.

The figures are not exhaustive and do not limit the present disclosure to the precise form disclosed.

DETAILED DESCRIPTION

Some embodiments of the disclosed technology provide a lens having four zones: an Optic Zone, a Peripheral Corneal Zone, a Clearance Control Zone and a Scleral Landing Zone. Various embodiments ensure full corneal and limbal clearance by the empirical selection of a base curve radius in the Optic Zone that approximates the radius of the underlying cornea; providing a Peripheral Corneal Zone using corneal topography or biometric mean height data; providing a Clearance Control Zone that is used to regulate the height of the lens above the cornea while normalizing the volume between the zone and the underlying eye; and, providing a novel universal Scleral Landing Zone that spreads lens mass over the underlying sclera without the need to regulate its geometry by modulating radius or angle for the purpose of controlling edge lift or limbal clearance. In this manner, the lens may always have corneal and limbal clearance while having mechanical-trauma-free scleral contact.

Embodiments of the disclosed technology may provide a scleral contact lenses for wearing on the anterior ocular surface, and methods for defining the scleral contact lenses using single parameter control geometry. These techniques may employ spline mathematics or other geometry to determine the surface contour of a contact lens at predetermined control points or knots on the posterior surface of the lens defined by their specified semi-chord radial distances from the center of the lens to the edge of the lens and their sagittal depth from a reference plane. Some embodiments employ the corneal topography of each eye to apply algorithms for determining the semi-meridian sagittal depth at one or more control points to allow for empirical ordering and observational fitting of an eye for the determination of the single parameter of Clearance Control Zone depth.

In some implementations, the base curve radius of the Optic Zone is selected using the apical radius of the cornea measured by standard keratometry or using the reference sphere or best fit sphere measured by corneal topography. The base curve geometry may be spherical, toric, aspherical by use of a conic constant, multifocal, or rotationally asymmetric for the purpose of correcting higher order aberrations or irregularity of the anterior corneal surface.

Furthermore, the Peripheral Corneal Zone may be empirically determined using elevation data from corneal topography or may be empirically determined using the radius of the base curve or effective radius of the base curve. The algorithm may employ an inverse relationship where the shorter the base curve radius, the shallower the knot at the peripheral aspect of the Peripheral Corneal Zone is set; and conversely, the longer the base curve radius the deeper the knot at the peripheral aspect of the Peripheral Corneal Zone is set.

Clinical observations were gathered for a large population of eyes with irregular corneas for which scleral contact lenses were required. The observations revealed an unexpected trend where eyes with short apical radii did not maintain the short radius in the corneal periphery and eyes with irregular corneas with long apical radii manifested a zone with a short radius outside the central zone having a long radius. These observations support the empirical method for determining the elevation of the peripheral knot in the Peripheral Corneal Zone in the absence of corneal topography elevation data.

The Clearance Control Zone depth of the disclosed scleral contact lens may be the only parameter that must be selected by observation. The desired pre-compression apical clearance for scleral lenses is commonly reported as 250 to 350 microns. The range of conjunctival compression is understood to be 80 to 120 microns or about 100 microns. A resultant post compression apical clearance of about 150 to 250 microns is considered by those skilled in the art as optimum. Embodiments of the disclosed technology address this understanding and allow for modification if the teaching of optimum post conjunctival compression objectives changes over time.

Some embodiments of the present invention may provide enhancement for maintaining limbal clearance post compression and address problems of bubble formation in the Clearance Control Zone that straddles the corneal-scleral junction or limbus of the eye. A knot within the Clearance Control Zone may be vertically or laterally positioned as a function of the depth of the zone.

In some embodiments at least one knot within the Clearance Control Zone may be moved vertically or laterally to control the area within at least one semi-meridian of the posterior surface and the underlying eye within the zone. The knot may be moved inward toward the center of the lens or downward toward the corneal surface when the Clearance Control Zone depth is greater and the knot may be moved outward away from the center of the lens or upward away from the corneal surface when the Clearance Control Zone depth is shallower.

In some embodiments, the Clearance Control Zone depth may vary in two or more semi-meridians to accommodate the circumferential elevation differences of an eye to be fit with the disclosed scleral contact lens. The difference in depths may be in semi-meridians that are 90 degrees apart, 180 degrees apart or any number of degrees apart. Ocular contour data suggest that the deepest area of the sclera and the shallowest area, as a rule, are not 90 degrees apart. Ocular contour data also suggests that the mean difference in elevation of the sclera at a chord of 14 mm is greater than 200 microns.

In some embodiments, the Clearance Control Zone is designed with a circumferential depth difference between 100 and 400 microns. In some embodiments the Clearance Control Zone is designed with circumferential depth differences between 150 and 300 microns. In some embodiments the circumferential depth differences are not orthogonal wherein the deepest and shallowest areas are 90 degrees apart; rather, the circumferential depth differences represent a sector where at least one sector of less than 90 degrees varies in depth from the Clearance Control Zone depth of the remainder of the Zone circumferentially and reconciles to the depth of the remainder of the lens in a transverse manner.

The disclosed universal Scleral Landing Zone design may be designed to solve the needs for one or more of: a) clearance at the medial aspect of the zone; b) edge lift at the peripheral aspect of the zone; c) allowance for compression into the conjunctiva of 80 to 120 microns; or d) a width between 0.8 and 2.5 mm. The optimum radius may be calculated using the formula for determining the radius of an arc when the width and the height of the arc are known: $R=h/2+W^2/8h$; R denoting the radius for the arc, h denoting the height of the arc and W, denoting the width of the arc. For example, if the width of the universal Scleral Landing Zone equals 1.8 mm and the desired height of the arc allowing for conjunctival compression and edge lift above the conjunctiva equals 0.130 mm (130 microns), solving for $Rmm=(0.130/2)+(1.8)^2/(8\times0.130)=3.18$ mm. Unexpectedly, this value is far shorter than the convex to the eye radius used by any commercial lens manufacturer or reported in published literature.

In some embodiments the overall diameter of the lens may be selected based on the horizontal visible iris diameter or corneal diameter. The diameter may range from 13.0 mm to 22.0 mm. A fixed diameter between 16.0 and 18.0 mm may be selected. For example, an overall diameter of 16.6 mm may allow for fitting a large number of the distribution of human eyes.

In some embodiments of the present invention the scleral contact lens may have a base curve radius from 5.0 mm to 12 mm, an Optic Zone diameter in the range of 5.0 to 10.0 mm, a Peripheral Corneal Zone width in the range of 0.2 to 2.0 mm; a Clearance Control Zone width in the range of 0.5 to 2.0 mm, and universal Scleral Landing Zone width in the range of 1.0 to 2.5 mm.

FIG. 1 illustrates a plan view of a scleral contact lens 100 according to some embodiments of the disclosed technologies. Referring to FIG. 1, the scleral contact lens 100 may have four zones and 6 control points or knots on the posterior surface. The most central zone is the Optic Zone OZ that has a surface shape to achieve optical correction of the eye when coupled with the anterior surface shape. The posterior surface shape of the Optic Zone may be spherical, aspherical with a conic constant, toric, multifocal with two or more radii, or rotationally asymmetrical to correct for corneal irregularity or higher order aberrations. The Optic Zone OZ may have a diameter that may be fixed or that may vary with its radius. The Optic Zone circumference is bounded by a control point CPI or knot 1 (k1) in each semi-meridian. The zone peripheral to the Optic Zone OZ may be the Peripheral Corneal Zone PCZ.

The Peripheral Corneal Zone PCZ may be bounded at its peripheral aspect by a control point CP2 or knot 2 (k2). The elevation of k2 is modulated as a function of the base curve radius where the shorter the base curve radius the shallower k2 is placed and the longer the base curve radius the deeper k2 is placed. For example, the sagittal depth of k2 for a base curve radius of 8.00 mm may not deviate from the extension of the same surface to the chord diameter of k2 by way of the same radius of curvature, 8.00 mm, continuing to the chord diameter of k2; while, as base curve radii decrease from 8.00 mm k2 may rise above the extension of the respective radius to the chord diameter of k2; and as base curve radii increase from 8.00 mm, k2 may fall below the extension of the respective radius to the chord diameter of k2.

The zone peripheral to the Peripheral Corneal Zone PCZ is the Clearance Control Zone CCZ. The Clearance Control Zone 103 is bounded at its peripheral aspect by a control point CP4 or knot 4 (k4) and may have at least one control point CP3 or knot 3 (k3) within the zone. The z-axis position of k4 relative to the z-axis position of k2 determines the Clearance Control Zone depth. The Clearance Control Zone depth may be the single parameter determined by observation of a predicate lens in the absence of ocular contour data for an eye. CP3 (k3) may be modulated in a relatively inward or downward direction or outward or upward direction as a function of the Clearance Control Zone depth; whereby, the greater the depth CP3 (k3) is moved inward toward the center of the lens or downward toward the underlying eye and the shallower the depth CP3 (k3) is moved outward toward the edge of the lens or upward away from the underlying eye.

The zone peripheral to the Clearance Control Zone CCZ is the Scleral Landing Zone SLZ. The Scleral Landing Zone is bounded at its peripheral aspect by a control point CP6 or knot 6 (k6) where the edge terminus is formed and has at least one control point CPS or knot 5 (k5) within the zone at its point of maximum depth. The Scleral Landing Zone SLZ may have a convex to the eye spherical geometry or may be formed as part of a cubic spline, basis spline or Bezier function, or the like generated by the positions of the series of knots. The positions of the knots k4, k5 and k6 may first be estimated by the calculation of the radius of an arc of known width and desired height according to the present invention.

It should be appreciated that the embodiments of FIG. 1 may be used, wholly or partially, in conjunction with other embodiments described herein.

Figure 2:
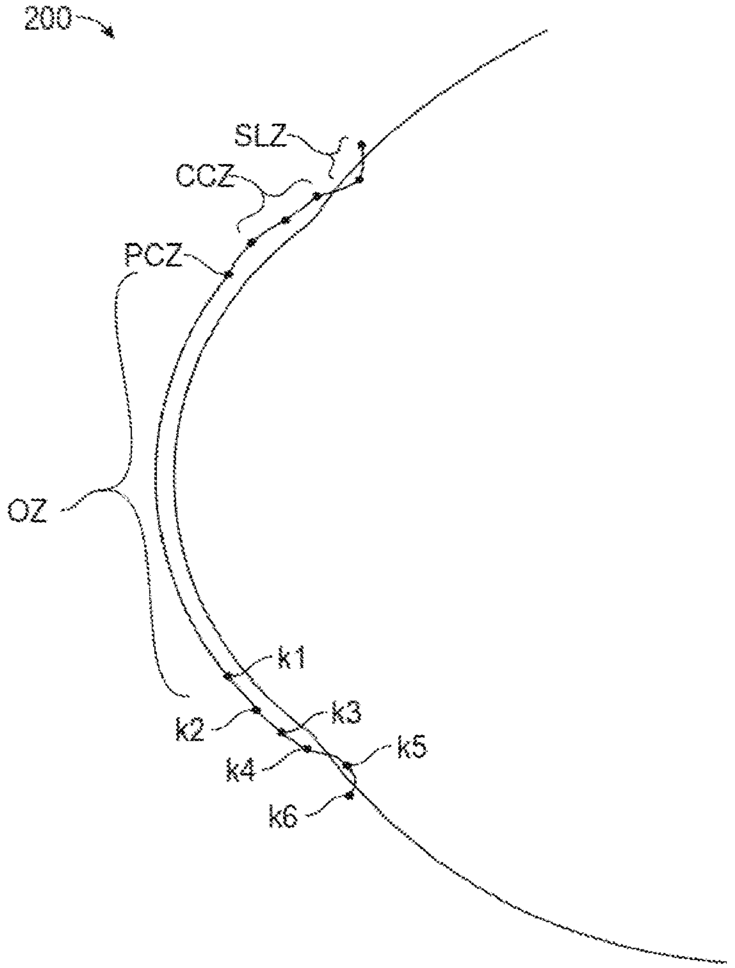
FIG. 2 illustrates a cross section view of the posterior surface of a scleral contact lens of the present invention showing knots and zones and an underlying ocular surface.

FIG. 2 illustrates a cross section view of the posterior surface of a scleral lens 200 according to some embodiments of the disclosed technologies. Referring to FIG. 2, knots k1-k6 are shown, as well as zones OZ, PCZ, CCZ, and SLZ.

Figure 3A:
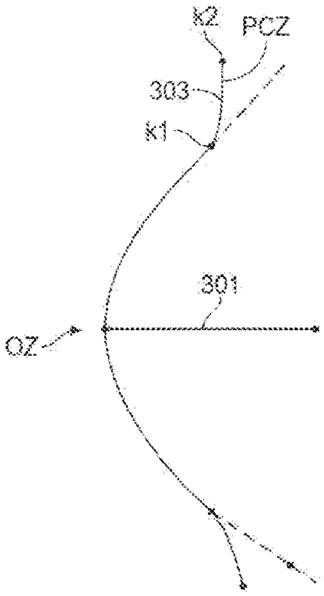
FIG. 3A illustrates a short radius base curve in an Optic Zone with a shallow Peripheral Corneal Zone.
Figure 3B:
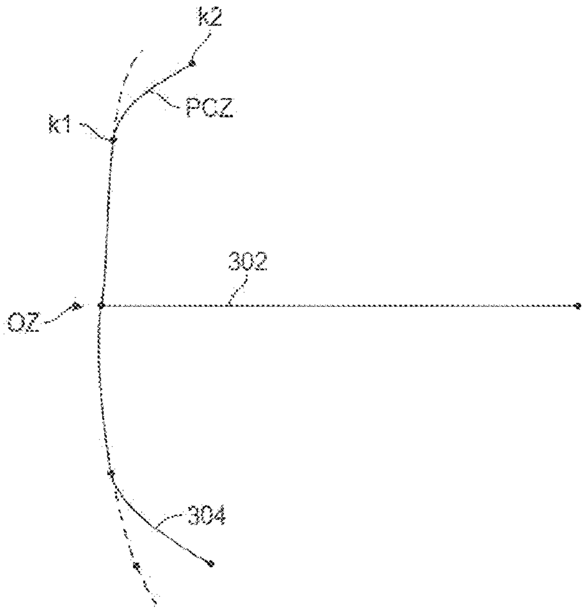
FIG. 3B illustrates a long radius base curve in an Optic Zone with a deep Peripheral Corneal Zone.

FIG. 3A illustrates a short base curve radius 301 in an Optic Zone 300 with a shallow Peripheral Corneal Zone 303. The Peripheral Corneal Zone 303 is bounded by CPI or knot 1 (k1) at its medial or central aspect and CP 2 or knot 2 (k2) at its peripheral aspect. FIG. 3B illustrates a long base curve radius 302 in an Optic Zone 300 with a deep Peripheral Corneal Zone 304. The Peripheral Corneal Zone 304 is bounded by CPI or knot 1 (k1) at its medial or central aspect and CP 2 or knot 2 (k2) at its peripheral aspect. The elevation of CP2 (k2) is modulated as a function of the base curve radius 300 where the shorter the base curve radius the shallower k2 is placed and the longer the base curve radius 300 the deeper k2 is placed. It should be appreciated that the embodiments of FIG. 3 may be used, wholly or partially, in conjunction with other embodiments described herein. For example, the sagittal depth of k2 for a base curve radius of 8.00 mm may not deviate from the extension of the same surface to the chord diameter of k2 by way of the same radius of curvature, 8.00 mm continuing to the chord diameter of k2; while, as base curve radii decrease from 8.00 mm k2 may rise above the extension of the respective radius to the chord diameter of k2; and as base curve radii increase from 8.00 mm, k2 306 may fall below the extension of the respective radius to the chord diameter of k2.

Figure 4A:
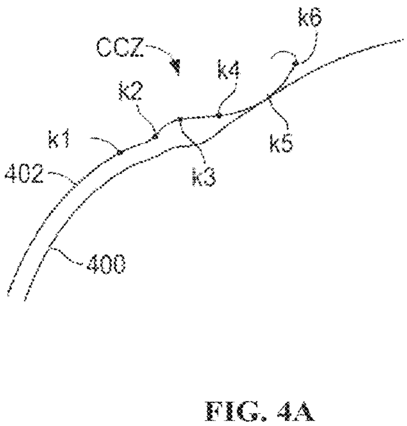
FIG. 4A illustrates a shallow Clearance Control Zone with a central knot shifted to increase the area between the meridian of the lens and the underlying eye within the zone.
Figure 4B:
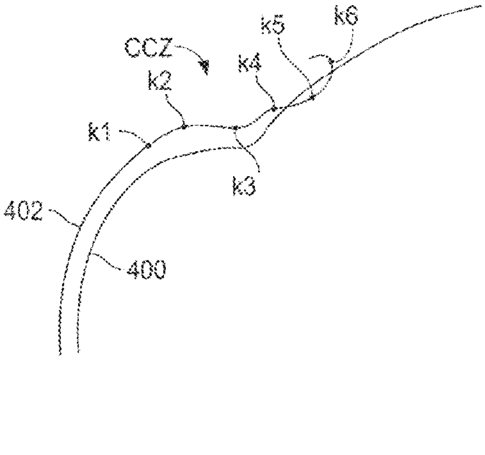
FIG. 4B illustrates a deep Clearance Control Zone with a central knot shifted to decrease the area between the meridian of the lens and the underlying eye within the zone.

FIG. 4A illustrates a shallow Clearance Control Zone with a CP3 (k3) shifted, outward, upward, or both, to increase the area between the meridian of the lens and the underlying eye 400 within the zone. FIG. 4B illustrates a deep Clearance Control Zone with a CP3 (k3) shifted, inward, downward, or both, to decrease the area between the meridian of the lens 402 and the underlying eye 400 within the zone. CP3 (k3) is modulated in a relatively inward/downward or outward/upward direction as a function of the Clearance Control Zone depth; whereby, the greater the depth CP3 (k3) is moved inward toward the center of the lens or downward toward the underlying eye and the shallower the depth CP3 (k3) is moved outward toward the edge of the lens or upward away from the underlying eye. It should be appreciated that the embodiments of FIG. 3 may be used, wholly or partially, in conjunction with other embodiments described herein.

Figures 5A, 5B, 5C:
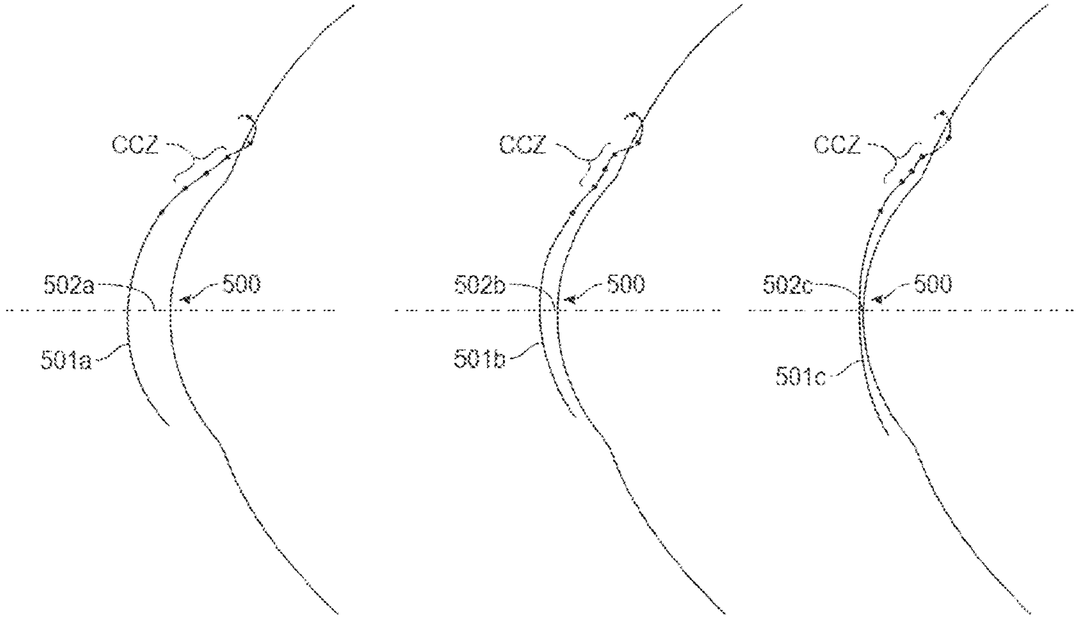
FIGS. 5A, 5B and 5C illustrate three lens surfaces to eye relationships; excess apical clearance; proper apical clearance; and inadequate apical clearance with apical touch respectively.

FIG. 5A illustrates a deep posterior lens surface **501*a* to eye 500 relationship where the clearance 502*a* between the posterior lens surface and the apex of the cornea is too great. For example, this illustration represents a clearance 502*a* of about 500 microns between the lens surface 501*a* and the apex of the cornea 500. This observation indicates the Clearance Control Zone depth should be reduced by at least 250 microns. FIG. 5B illustrates a proper lens surface 501*b* to the apex of the cornea 500 relationship wherein the clearance 502*b* is in the desired range of 150 to 250 microns. FIG. 5C illustrates a shallow posterior lens surface 501*c* to eye 500 relationship wherein the clearance 502*c* between the posterior lens surface 501*c* and the apex of the cornea 500** is inadequate. This observation indicates the Clearance Control Zone depth should be increased by at least 200 microns.

Figure 6:
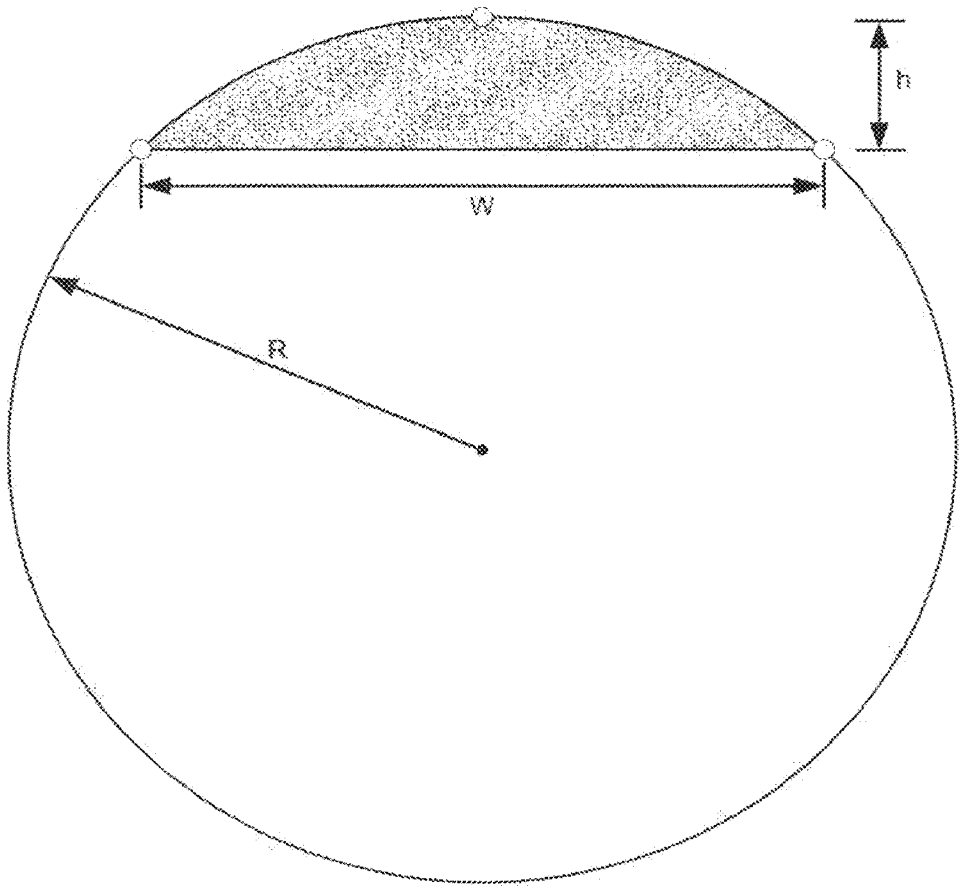
FIG. 6 is the model for determining the radius of an arc when the width and depth of the arc are known for use in calculating the universal Scleral Landing Zone radius.

FIG. 6 illustrates the model for determining the radius of an arc when the width and depth of the arc are known. This model may be used in calculating the universal Scleral Landing Zone radius. The optimum radius may be calculated using the formula for determining the radius of an arc when the width and the height of the arc are known. The formula is $R=h/2+W^2/8h$, where R denotes the radius for the arc, h denotes the height of the arc, and W denotes the width of the arc, as shown in FIG. 6.

Figure 7:
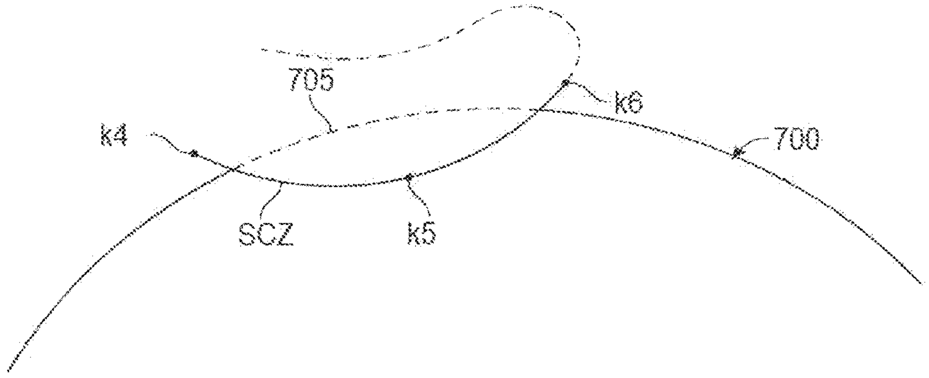
FIG. 7 illustrates the universal Scleral Landing Zone on an underlying sclera post conjunctival compression.

FIG. 7 illustrates a cross section of the universal Scleral Landing Zone SLZ with CP4 (k4), CPS (k5), and CP6 (k6) on an underlying sclera 700 post conjunctival compression. The CP4 knot 4 (k4) medial aspect and the CP6 knot 6 (k6) peripheral aspect of the Scleral Landing Zone SLZ are anterior to the ocular surface 700 while CPS knot 5 (k5) midpoint of the Scleral Landing Zone SLZ is at the point of greatest compression into the ocular surface under the Scleral Landing Zone SLZ. The pre-compression ocular surface 705 and post compression ocular surface, which coincides with the SLZ in FIG. 7, reflects the amount of the expected conjunctival compression with a scleral contact lens. The illustration represents the manner that the short convex to the eye radius of curvature provides edge lift and provides the desired medial aspect clearance after the scleral contact lens compresses the conjunctiva under the scleral landing zone SLZ.

Figure 8:
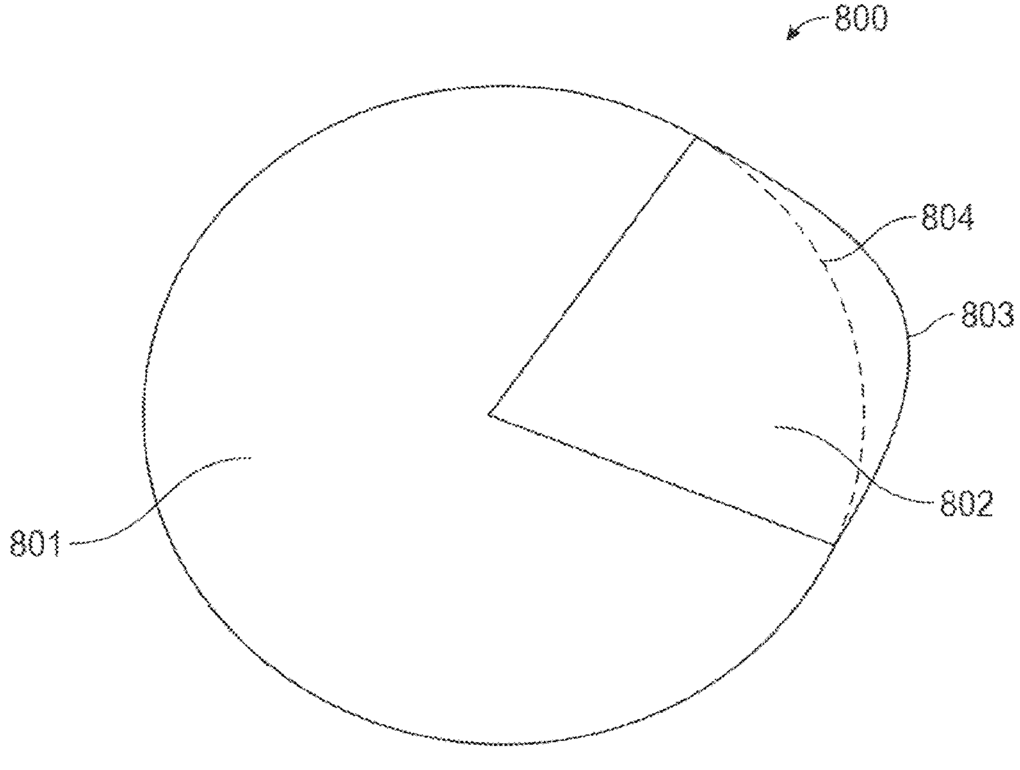
FIG. 8 illustrates a non-orthogonal sector of a scleral contact lens with asymmetric elevation.

FIG. 8 illustrates a plan view of a non-orthogonal sector of a scleral contact lens 800 with asymmetric elevation. The large sector 801 of the lens 800 represents the angular region of the lens having a uniform Clearance Control Zone depth and resultant total depth at the midpoint of the universal Scleral Landing Zone. The smaller sector 802 of the lens 800 represents a region having a shallower depth than sector 801. The lens surface changes in elevation in a transverse manner from the most shallow depth to the greater depth to allow the surface to be seamless and smooth and without step changes in elevation. There may be more than one angular sector of greater or lesser Clearance Control Zone depth to accommodate ocular contour differences. The finished lens with a sector of unequal Clearance Control Zone depth may be planar and not round as illustrated by the path of the perimeter 803 of the lens; or the finished lens with a sector of unequal Clearance Control Zone depth may be round but not planar as illustrated by the path of the perimeter 804. In this manner an edge reconciliation zone is not required to make the lens edge planar and round.

The posterior surface parameters of the disclosed single parameter control universal landing zone scleral contact lens apparatus may be calculated manually from input data or more efficiently with a computer program product. The steps include: a) use of a the horizontal visible iris diameter or corneal diameter to determine the overall diameter of the scleral contact lens; b) scaling the width of the zones for the overall diameter; c) determining the base curve radius from the measurement of the apical radius of the cornea from keratometry or the reference sphere from corneal topography; d) determining the elevation of k2 from the selected base curve radius; e) determining the Corneal Clearance Zone depth from the single observation of apical clearance from a predicate lens applied to an eye or from a measured scleral sagittal depth at a chord outside the cornea; f) determining the lateral or sagittal movement of k5 from the Corneal Clearance Zone depth value to optimize the volume between the posterior surface of the lens within the Corneal Clearance Zone and the underlying eye.

The parameters of the anterior surface of the lens may be derived by usual and customary means and may be calculated manually from input data or more efficiently with a computer program product by: a) adding an anterior optic zone radius or radii that creates the desired lens power in concert with the posterior surface of the optic zone and the post lens tear lens; b) selecting an anterior optic zone diameter as a function of lens power to control the center thickness and junction thickness; c) employing thickness rules for the remainder of the annular zone outside the anterior optic zone to create a thickness profile that manages lens flexure, lens breakage and the lid to lens relationship to optimize comfort.

Figure 9:
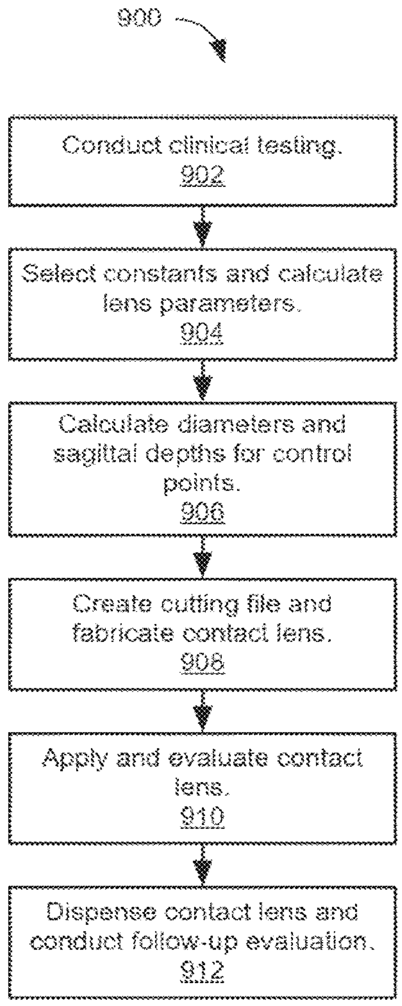
FIG. 9 is a flowchart illustrating an overview process for producing a scleral contact lens according to some embodiments of the disclosed technologies.

FIG. 9 is a flowchart illustrating an overview process 900 for producing a scleral contact lens according to some embodiments of the disclosed technologies. The elements of the process 900 are presented in one arrangement. However, it should be understood that one or more elements of the process may be performed in a different order, in parallel, omitted entirely, and the like. Furthermore, the process 900 may include other elements in addition to those presented.

Referring to FIG. 9, the process 900 may include conducting clinical testing of the eye, at 902. The clinical testing may include determination of unaided visual acuity, refraction, binocular vision, eye health, keratometry, corneal diameter, corneal topography, lid position and aperture size, pupillometry, observation of the apical corneal clearance of a predicate scleral contact lens of known parameters, and the like.

The process 900 may include selecting constants and calculating lens parameters, at 904. These may include base curve radius, optic zone diameter, overall diameter, Peripheral Corneal Zone width, sagittal depth of k2, Clearance Control Zone width, Corneal Clearance Zone depth, lateral and sagittal position of k3, Scleral Landing Zone width, sagittal depth of k5, lens power, and the like.

The process 900 may include calculating diameters and sagittal depths for control points and/or knots of the posterior surface of the contact lens, at 906. These calculations may be based on biometric mean data, measured corneal topography, or the like, or combinations thereof. These calculations are described in detail below. Following these calculations, control points and/or knots for the anterior surface may be calculated, for example using thickness rules or constants from one or more of the posterior surface control points to one or more of the anterior surface control points and incorporating the required anterior central radius or radii of curvature to produce the desired lens power or powers in the event of multifocal optics, or the like.

The process 900 may include creating a cutting file and fabricating a contact lens, at 908. For example, a semi-meridian for the posterior surface of the contact lens may be calculated using the control points or knots, for example as shown in FIG. 2. The semi-meridian surface may be generated using splines, geometric segments, or the like, or combinations thereof. The contact lens may be fabricated with usual and customary good manufacturing practices from standard rigid gas permeable material, or the like. For example, a polish-free computer numerically controlled lathe may be employed to cut the contact lens. Cutting may be followed by a contour inspection of the posterior surface of the contact lens to determine the finished posterior surface matches the intended shape.

The process 900 may include applying and evaluating the contact lenses, at 910. This may include capturing an image of the contact lens on the eye of the patient. The image may be analyzed to assess the lens-eye relationship and to measure lens centration. The evaluation may include steps to determine the over-refraction, to measure visual acuity, and the like. The process 900 may conclude with dispensing the contact lens, and conducting one or more follow-up evaluations, at 912.

Figure 10:
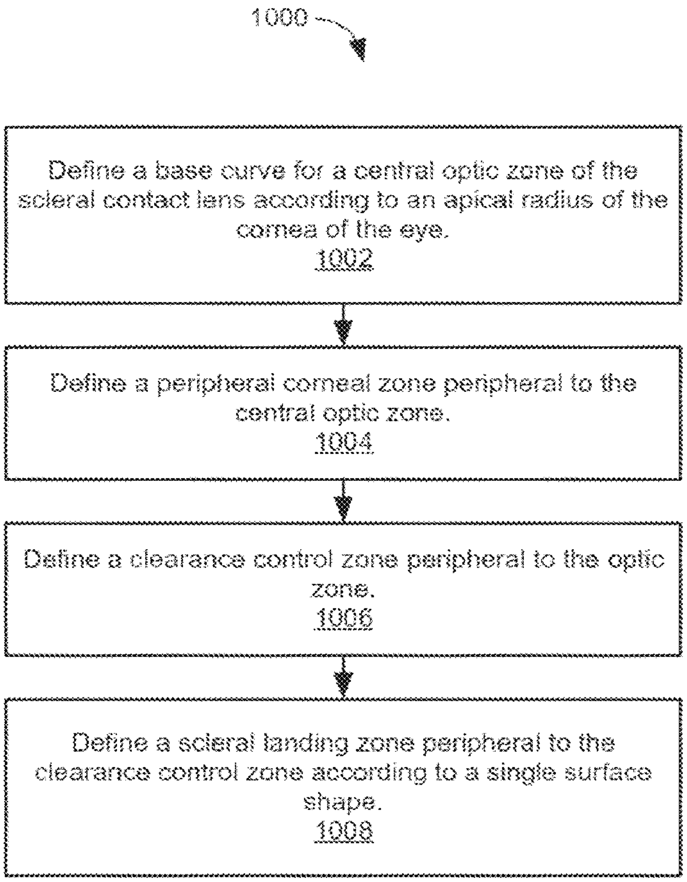
FIG. 10 is a flowchart illustrating an overview process for defining a shape of a posterior surface of a scleral contact lens for an eye of a patient according to some embodiments of the disclosed technologies.

FIG. 10 is a flowchart illustrating an overview process 1000 for defining a shape of a posterior surface of a scleral contact lens for an eye of a patient according to some embodiments of the disclosed technologies. The elements of the process 1000 are presented in one arrangement. However, it should be understood that one or more elements of the process may be performed in a different order, in parallel, omitted entirely, and the like. Furthermore, the process 1000 may include other elements in addition to those presented.

Referring to FIG. 10, the process 1000 may include defining a base curve for a central optic zone of the scleral contact lens according to an apical radius of the cornea of the eye, at 1002. The base curve of the optic zone may be defined according to at least one of a spherical radius, an aspherical radius with a conic constant, a torus, a multifocal shape, or a rotationally asymmetric shape.

The process 1000 may include defining a peripheral corneal zone peripheral to the central optic zone, at 1004. The process 1000 may include defining a clearance control zone peripheral to the optic zone, at 1006. The process 1000 may include defining a scleral landing zone peripheral to the clearance control zone according to a single surface shape, at 1008. The peripheral corneal zone, the clearance control zone, and the scleral landing zone may be defined according to according to a spline having a plurality of knots and/or control points.

The peripheral corneal zone may be defined according to a peripheral most knot and a medial most knot. The peripheral most knot may be shallower in sagittal depth than the medial most knot relative to a continuation of the base curve to the semi-chord diameter of the peripheral most knot when the base curve radius is shorter than a predetermined length. Alternatively, the peripheral most knot may be deeper in sagittal depth than the medial most knot relative to the continuation of the base curve to the semi-chord diameter of the peripheral most knot when the base curve radius is longer than the predetermined length. In some embodiments, the predetermined length is 8.0 mm.

The clearance control zone may be defined according to at least one knot within the clearance control zone. A location of the at least one knot may be selected to control an area between the posterior surface of the clearance control zone and the underlying surface of the eye in at least one semi-meridian.

In some embodiments, a convex to the eye radius of the scleral landing zone may be less than 10 mm. In some embodiments, the scleral landing zone may be defined according to at least one knot of a spline that is equivalent in depth to a convex to the eye radius of less than 10 mm. In some embodiments, the scleral landing zone may be defined according to at least one knot of a spline that is equivalent in depth to a convex to the eye radius of less than 5 mm.

Table 1 presents the clinical measures that may be used to determine the parameters of the disclosed scleral lens in conjunction with antecedent parameters that may be used to determine additional parameters. The single posterior surface parameter that may be determined by observation of a predicate lens is the Clearance Control Zone depth. All other parameters may be selected or calculated empirically from clinical measurements and predicate parameter selection rules.

TABLE 1

Example of Empirical System for Calculating Scleral Lens Parameters from Clinical Markers and Predicate Lens Parameters

| Antecedent Clinical Measurement | Predicate Lens Parameter | Lens Parameter | Nominal Value | Algorithm Rule for each of 3 overall diameters |
|---|---|---|---|---|
| Horizontal Visible Iris Diameter or Corneal Diameter | | Overall Diameter (OAD)<br>k6 chord location | 16.6 mm | less than 11.5 = 15.5;<br>11.5 to 12.1 = 16.6;<br>above 12.1 = 17.7 |
| | Overall diameter (OAD) | Chord diameter of k2 | 10.4 mm | 15.5 mm OAD = 10.1 mm<br>16.6 mm OAD = 10.4 mm<br>17.7 mm OAD = 10.7 mm |
| | Overall diameter (OAD) | Chord diameter of k4 | 13.2 mm | 15.5 mm OAD = 12.7 mm<br>16.6 mm OAD = 13.2 mm<br>17.7 mm OAD = 13.7 mm |
| | Overall diameter (OAD) | Chord diameter of k5 | 14.9 mm | 15.5 mm OAD = 14.1 mm<br>16.6 mm OAD = 14.9 mm<br>17.7 mm OAD = 15.7 mm |
| | Overall diameter (OAD) | Chord diameter of k6 | 16.4 mm | 0.2 mm less than OAD |
| | Overall diameter (OAD) | Effective radius of Scleral Landing Zone | 3.18 mm | 15.5 mm OAD = 1.95 mm<br>16.6 mm OAD = 3.18 mm<br>17.7 mm OAD = 3.91 mm |
| | Overall diameter (OAD) | Sagittal depth of k6 from lens geometric center | 4.405 mm | Sagittal depth of the mean eye at chord of k6 plus 150 microns. |
| Apical Corneal Radius or best fit sphere or Reference sphere | | Base curve radius (BCR) | 8.0 mm | 0.2 mm longer than apical radius; mean apical radius = 7.80 mm |
| | Base curve radius (BCR) | Optic Zone diameter = Chord diameter of k1 | 8.0 mm | 0.2 longer than apical radius |
| | Base curve radius (BCR) | Sagittal depth of k2 of PCZ from lens geometric center | 1.920 mm | Adjusted by inverse of 25 microns per 0.1 mm deviation of BCR from 8.0 mm from sag of BCR at chord diameter of k2 |

TABLE 1-continued

Example of Empirical System for Calculating Scleral Lens Parameters from Clinical Markers and Predicate Lens Parameters

| Antecedent Clinical Measurement | Predicate Lens Parameter | Lens Parameter | Nominal Value | Algorithm Rule for each of 3 overall diameters |
|---|---|---|---|---|
| Clearance Control Zone Depth observation | | Clearance Control Zone Depth (k4 − k2) | 1.300 mm | Increases by microns of observed inadequate clearance and decreases by microns of excess clearance in 25 micron steps |
| | Clearance Control Zone Depth | Sagittal depth of k4 from lens geometric center | 3.220 mm | 250 microns deeper than mean eye at k4 chord |
| | Clearance Control Zone Depth | Clearance Control Zone volume; Radial and sagittal position of k3 | 5.90 mm/ 2.237 mm | Calculated to produce no radial clearance from mean eye greater than 150 microns throughout the zone |
| | Sagittal Depth of k4; effective radius of K5 | Sagittal depth of k5 | 3.914 mm | Depth of the arc with the effective radius calculated using the assumed compression and the width of the Scleral Landing Zone |
| Manifest refraction or lens over-refraction | BCR | Lens power and anterior optic zone radius of curvature | 8.60 mm | Usual and customary radius calculation using lens index of refraction and vertex distance adjusted |
| | Lens power | Anterior optic zone diameter | 8.4 mm | Decreases as plus and minus lens power increases to maintain constant harmonic thickness of optic zone |
| | Overall diameter (OAD) | Center thickness and thickness profile | 0.32 mm | Harmonic thickness until taper outside of cornea; thickness increases and decreases in proportion to OAD |

In one embodiment, the horizontal visible iris diameter or corneal diameter may be the first clinical measure used to determine the overall diameter of the scleral contact lens. The overall diameter may be calculated using a mathematical method or determined by a look up table as presented in Table 1. The overall diameter may be used as a predicate parameter to select the sagittal depth of a predicate lens for observation; to select the chord diameter of knot 2 k2; to select the chord diameter of knot 4 k4; to select the chord diameter of knot 5 k5; to select the knot diameter of k6; and to calculate the effective radius of the universal scleral landing zone; and the knot locations on the anterior surface of the lens to create the thickness profile of the lens.

The apical radius of the cornea or the best fit sphere or reference sphere from automated corneal topography may be the second clinical measure and used to derive the base curve radius of the posterior optic zone of the scleral lens. In one embodiment, the base curve radius may be calculated to be 0.2 mm longer than the apical radius or best fit or reference sphere. The derived base curve radius may in turn be used to calculate the posterior optic zone diameter and the sagittal depth of knot 2 from the plane of the geometric center of the posterior surface of the scleral contact lens.

The observation of the apical clearance with at least one predicate contact lens of known parameters may be the third clinical measure used to derive parameters of the scleral lens. The clearance observation may be used to increase or decrease a selected sagittal depth of the Clearance Control Zone depth parameter of a lens to be manufactured for the respective eye. The resultant Clearance Control Zone depth may in turn be used to calculate a horizontal and/or sagittal depth position of knot 3 k3 in the Clearance Control Zone for the purpose of regulating the area between the posterior surface of the lens and the underlying eye in at least one semi-meridian of the Clearance Control Zone or the volume under the Clearance Control Zone of the lens and the underlying eye circumferentially by calculations of the position of k3 in multiple semi-meridians.

A manifest refraction may be used to empirically calculate lens power by integrating the manifest refraction with the selected base curve radius and measured apical corneal radius. Alternatively, an over-refraction may be conducted by placing a predicate scleral lens of known base curve radius and power on an eye to determine a final lens power by integrating the over-refraction with the base curve radius of the predicate lens, the power of the predicate lens and the new base curve radius derived from the apical radius of the cornea.

The final lens power parameter may be used to determine the anterior optic zone radius of curvature. The lens power created by the posterior optic zone radius, the anterior optic zone radius and the index of refraction of the material may be used to determine the anterior optic zone diameter for the purpose of controlling the harmonic thickness of the scleral contact lens within the anterior optic zone.

Table 2 presents the steps for determining the posterior surface parameter values as an example of an embodiment of the disclosed scleral contact lens. Clinical measurements and the single observation of apical clearance with a predicate lens of known parameter values in the diameter determined by the corneal diameter of an eye to be observed with the predicate lens. Table 2 presents sample design rules as an example of one embodiment of the disclosed scleral contact lens along with nominal values for the parameters of the lens.

TABLE 2

| Posterior Surface Design Step | Clinical measure Input | Antecedent Parameter Input | Example Clinical Input or Antecedent Parameter | Parameter Selected | Knot Number | Parameter Label | Semi-meridian radial distance (mm) | Pre-Compression Clearance (microns) | Post-Compression Clearance (microns) | Mean eye Elevation (mm) | Lens Knot Elevation (mm) | Example Parameter Selection Rule |
|---|---|---|---|---|---|---|---|---|---|---|---|---|
| 1 | Corneal diameter or horizontal visible iris diameter | | 11.8 mm | Overall Diameter and radial k2, k3*, k4, k5, k6 radial distances | 6 | OAD | 8.30 | | | | | less than 11.5 = 15.5; 11.5 to 12.1 = 16.6; above 12.1 = 17.7 |
| | | OAD | 16.6 mm | Radial distance of k2 | 2 | PCZ | 5.20 | | | | | 15.5 mm OAD = 10.1 mm 16.6 mm OAD = 10.4 mm 17.7 mm OAD = 10.7 mm |
| | | OAD | 16.6 mm | Radial distance of k3 | 3 | Volume Control Knot | 5.90* | | | | | Equals (k4 − k2)/2* may shift laterally to control volume in CCZ as a function of sagittal depth difference of k4 − k2; |
| | | OAD | 16.6 mm | radial distance of k4 | 4 | CCZ | 6.60 | | | | | 15.5 mm OAD = 12.7 mm 16.6 mm OAD = 13.2 mm 17.7 mm OAD = 13.7 mm |
| | | OAD | 16.6 mm | radial distance k5 | 5 | LZM | 7.40 | | | | | Equals (k6 − k4)/2 |
| | | OAD | 16.6 mm | radial distance k6 | 6 | LZ/OAD | 8.20 | | | | | Equals OAD - edge terminus width. 0.1 mm |
| 2 | Apical radius from keratometry or corneal topography | | 7.80 mm | Base Curve Radius (BCR) in mm | 1 | BCR | 8.00 | | | | | Equals keratometry, best fit sphere, or reference sphere value plus a constant. Example constant = 0.2 mm |
| | | BCR and k1 radial value | 8.00 mm | k1 radial distance | 1 | POZ radial location | 4.00 | | | | | Semi-meridian radial distance equals BCR in mm divided by two. |
| | | BCR and k1 radial value | 8.00 mm and 4.0 mm | k1 sagittal depth | 1 | POZ depth | 4.00 | Varies with BCR | 150 | 1.104 | 1.1072 | Sag of 8.00 mm spherical BCR at 4.0 semi chord |
| | | BCR and k2 radial value from step 1 | 8.0 mm and 5.20 mm | k2 sagittal depth | 2 | PCZ depth | 5.20 | 250 | 150 | 1.925 | 1.925 | Adjusted by inverse of 25 microns per 0.1 mm deviation of BCR from 8.0 mm from sag of BCR at chord diameter of k2 |
| 3 | Pre-compression Corneal Clearance observation with with lens of same OAD and mean knot locations | k2 radial distance, k2 depth and k4 radial distance from step 1 | 250 microns preferred and observed: k2 = 5.20 mm k4 = 6.60 mm | k4 sagittal depth | 4 | CCZ depth | 6.60 | 100 | 0 | 3.070 | 3.220 | Equals the sag of the eye plus the desired post compression apical clearance. Derived by observation of a predicate lens having mean parameters for the selected OAD. Depth adjusted in 25 micron steps inverse to observation of pre- |

TABLE 2-continued

| Posterior Surface Design Step | Clinical measure Input | Antecedent Parameter Input | Example Clinical Input or Antecedent Parameter | Parameter Selected | Knot Number | Parameter Label | Semi-meridian radial distance (mm) | Pre-Compression Clearance (microns) | Post-Compression Clearance (microns) | Mean eye Elevation (mm) | Lens Knot Elevation (mm) | Example Parameter Selection Rule |
|---|---|---|---|---|---|---|---|---|---|---|---|---|
| | | | | | | | | | | | | compression apical clearance |
| | | k2 and k4 radial value and k4 sagittal depth; biometric mean data | | k3 radial and sagittal location | 3 | VCK position | 5.90 | 250 | 150 | 2.487 | 2.237 | Calculated to produce no radial post-compression clearance from mean eye greater than 150 microns throughout the zone |
| | | k4 and k5 radial value and k4 sagittal depth | k4 = 6.60 mm/3.320, k5 = 7.45 mm | k5 sagittal depth | 5 | LZMD | 7.45 | 0 | −100 | 3.664 | 3.914 | Equals the sag of the eye plus the pre compression apical clearance. |
| | | k6 radial value | 8.20 mm | k6 sagittal depth | 6 | LZD | 8.20 | 100 | 0 | 4.255 | 4.405 | Equals the sag of the eye plus the desired post compression apical clearance. |

In some embodiments a computer program product may be used to accept the entry fields including the corneal diameter, apical corneal radius, Clearance Control Zone depth observation with a predicate lens of known parameters, parameters of the predicate lens and the manifest refraction or over refraction with a lens of known parameters. The computer program product may calculate the final scleral lens parameters using the clinical measurements, the resultant lens parameters from the clinical measurements, and the Clearance Control Zone depth observation to calculate final scleral lens parameters and cutting files for manufacturing.

Figure 11:
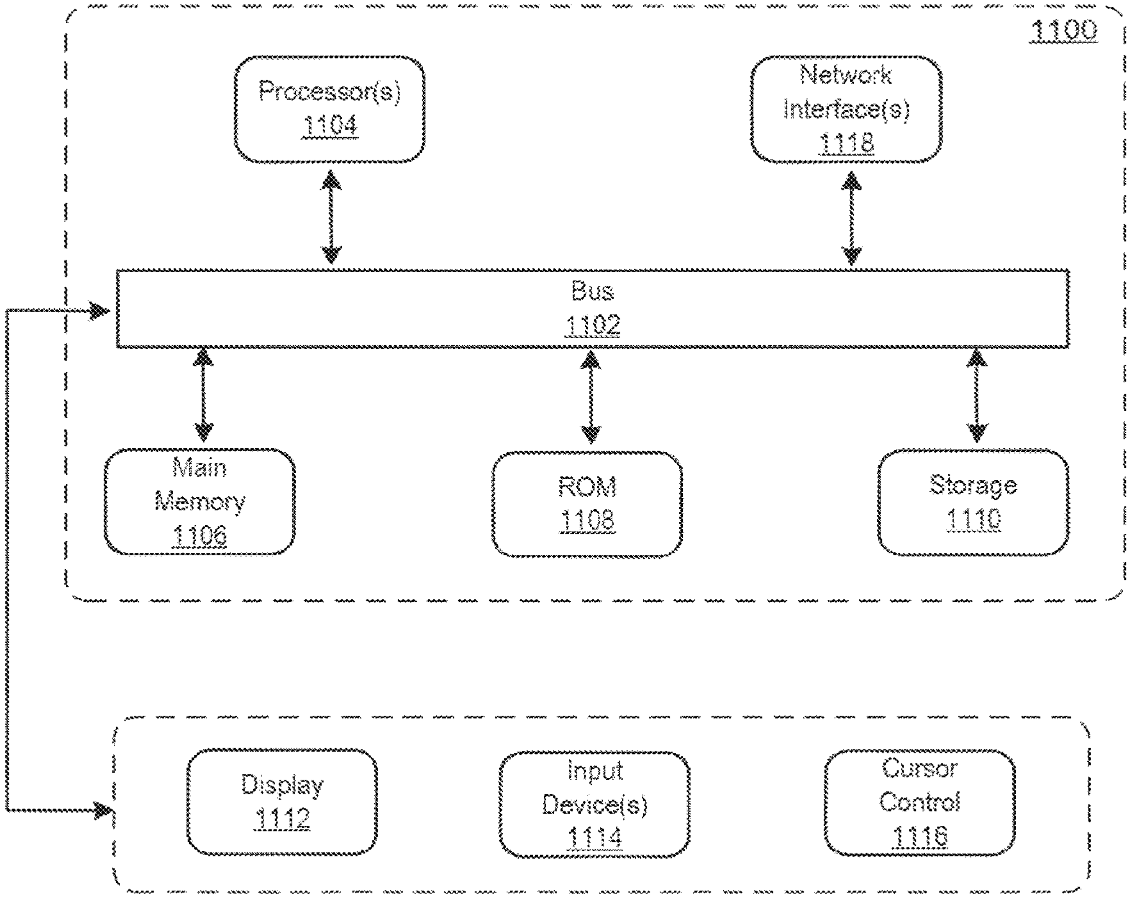
FIG. 11 depicts a block diagram of an example computer system m which embodiments described herein may be implemented.

FIG. 11 depicts a block diagram of an example computer system 1100 in which embodiments described herein may be implemented. The computer system 1100 includes a bus 1102 or other communication mechanism for communicating information, one or more hardware processors 1104 coupled with bus 1102 for processing information. Hardware processor(s) 1104 may be, for example, one or more general purpose microprocessors.

The computer system 1100 also includes a main memory 1106, such as a random access memory (RAM), cache and/or other dynamic storage devices, coupled to bus 1102 for storing information and instructions to be executed by processor 1104. Main memory 1106 also may be used for storing temporary variables or other intermediate information during execution of instructions to be executed by processor 1104. Such instructions, when stored in storage media accessible to processor 1104, render computer system 1100 into a special-purpose machine that is customized to perform the operations specified in the instructions.

The computer system 1100 further includes a read only memory (ROM) 1108 or other static storage device coupled to bus 1102 for storing static information and instructions for processor 1104. A storage device 1110, such as a magnetic disk, optical disk, or USB thumb drive (Flash drive), etc., is provided and coupled to bus 1102 for storing information and instructions.

The computer system 1100 may be coupled via bus 1102 to a display 1112, such as a liquid crystal display (LCD) (or touch screen), for displaying information to a computer user. An input device 1116, including alphanumeric and other keys, is coupled to bus 1102 for communicating information and command selections to processor 1104. Another type of user input device is cursor control 1116, such as a mouse, a trackball, or cursor direction keys for communicating direction information and command selections to processor 1104 and for controlling cursor movement on display 1112. In some embodiments, the same direction information and command selections as cursor control may be implemented via receiving touches on a touch screen without a cursor.

The computing system 1100 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 1100 may implement the techniques described herein using customized hard-wired logic, one or more ASICs or FPGAs, firmware and/or program logic which in combination with the computer system causes or programs computer system 1100 to be a special-purpose machine. According to one embodiment, the techniques herein are performed by computer system 1100 in response to processor(s) 1104 executing one or more sequences of one or more instructions contained in main memory 1106. Such instructions may be read into main memory 1106 from another storage medium, such as storage device 1110. Execution of the sequences of instructions contained in main memory 1106 causes processor(s) 1104 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1110. Volatile media includes dynamic memory, such as main memory 1106. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates m transferring information between non-transitory media. For example, transmission media includes coaxial cables, copper wire and fiber optics, including the wires that comprise bus 1102. Transmission media can also take the form of acoustic or light waves, such as those generated during radio-wave and infra-red data communications.

The computer system 110 also includes a communication interface 1118 coupled to bus 1102. Network interface 1118 provides a two-way data communication coupling to one or more network links that are connected to one or more local networks. For example, communication interface 1118 may be an integrated services digital network (ISDN) card, cable modem, satellite modem, or a modem to provide a data communication connection to a corresponding type of telephone line. As another example, network interface 1118 may be a local area network (LAN) card to provide a data communication connection to a compatible LAN (or a WAN component to communicate with a WAN). Wireless links may also be implemented. In any such implementation, network interface 1118 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 1118, which carry the digital data to and from computer system 1100, are example forms of transmission media.

The computer system 1100 can send messages and receive data, including program code, through the network(s), network link and communication interface 1118. In the Internet example, a server might transmit a requested code for an application program through the Internet, the ISP, the local network and the communication interface 1118.

The received code may be executed by processor 1104 as it is received, and/or stored in storage device 1110, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 1100.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

The invention claimed is:

1. A scleral contact lens for an eye of a patient, the scleral contact lens comprising:

an anterior surface; and a posterior surface, the posterior surface comprising:

a central optic zone defined by a base curve according to an apical radius of the cornea of the eye;

a peripheral corneal zone peripheral to the central optic zone, a clearance control zone peripheral to the peripheral corneal zone, and a universal scleral landing zone peripheral to the clearance control zone, the universal scleral landing zone having a single radius, landing zone angle and surface shape and a convex to the eye radius less than 10 mm that is not controlled by modulating an angle;

wherein the scleral contact lens is configured not to contact the cornea of the eye;

wherein the universal scleral landing zone is configured to contact the eye; and wherein the central optic zone, the peripheral corneal zone, and the clearance control zone are configured not to contact the eye.

2. The scleral contact lens of claim 1, wherein:

the single surface shape of the scleral landing zone has a spherical geometry.

3. The scleral contact lens of claim 1, wherein:

the single surface shape of the scleral landing zone is defined by at least one knot of a spline.

4. The scleral contact lens of claim 1, wherein:

the single surface shape of the scleral landing zone is defined by part of a cubic spline, basis spline, or Bezier function.

5. The scleral contact lens of claim 1, wherein:
the base curve of the optic zone is defined by at least one of a spherical radius, an aspherical radius with a conic constant, a torus, a multifocal shape, or a rotationally asymmetric shape.

6. The scleral contact lens of claim 1, wherein:
the peripheral corneal zone, the clearance control zone, and the scleral landing zone are defined by a spline having a plurality of knots and/or control points.

7. A method for defining a shape of a posterior surface of a scleral contact lens for an eye of a patient, the method comprising:
defining a base curve for a central optic zone of the scleral contact lens according to an apical radius of the cornea of the eye;
defining a peripheral corneal zone peripheral to the central optic zone;
defining a clearance control zone peripheral to the peripheral corneal zone; and
defining a universal scleral landing zone peripheral to the clearance control zone according to a single radius, landing zone angle and surface shape and a convex to the eye radius of less than 10 mm that is not controlled by modulating an angle;
wherein the scleral contact lens is configured not to contact the cornea of the eye;
wherein the universal scleral landing zone is configured to contact the eye; and
wherein the central optic zone, the peripheral corneal zone, and the clearance control zone are configured not to contact the eye.

8. The method of claim 7, wherein:
the single surface shape of the scleral landing zone has a spherical geometry.

9. The method of claim 7, further comprising:
defining the single surface shape of the scleral landing zone according to at least one knot of a spline.

10. The method of claim 7, further comprising:
defining the single surface shape of the scleral landing zone according to part of a cubic spline, basis spline, or Bezier function.

11. The method of claim 7, further comprising:
defining the base curve of the optic zone according to at least one of a spherical radius, an aspherical radius with a conic constant, a torus, a multifocal shape, or a rotationally asymmetric shape.

12. The method of claim 7, further comprising:
defining the peripheral corneal zone, the clearance control zone, and the scleral landing zone according to a spline having a plurality of knots and/or control points.

* * * * *